US010966726B2

(12) United States Patent
Lorenzo

(10) Patent No.: US 10,966,726 B2
(45) Date of Patent: Apr. 6, 2021

(54) BALLOON ASSIST DEVICE AND METHOD FOR USING THE SAME

(71) Applicant: DePuy Synthes Products, Inc., Raynham, MA (US)

(72) Inventor: Juan Lorenzo, Raynham, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 176 days.

(21) Appl. No.: 15/941,227

(22) Filed: Mar. 30, 2018

(65) Prior Publication Data

US 2019/0298385 A1   Oct. 3, 2019

(51) Int. Cl.
| | | |
|---|---|---|
| A61B 17/12 | (2006.01) | |
| A61M 25/10 | (2013.01) | |
| A61B 17/00 | (2006.01) | |
| A61B 17/02 | (2006.01) | |

(52) U.S. Cl.
CPC .... *A61B 17/12136* (2013.01); *A61B 17/1204* (2013.01); *A61B 17/12109* (2013.01); *A61M 25/10* (2013.01); *A61B 17/0218* (2013.01); *A61B 2017/00862* (2013.01)

(58) Field of Classification Search
CPC .............. A61M 25/1018; A61M 25/10; A61M 25/1025; A61B 17/13126; A61B 17/0218; A61B 17/1204; A61B 17/12109; A61B 17/12136; A61B 17/00296; A61B 2017/00296; A61B 2017/00862; A61B 2017/1205; A61B 25/10; A61B 20/1018; A61B 5/6853
USPC ....................................................... 606/194
See application file for complete search history.

(56) References Cited

U.S. PATENT DOCUMENTS

| | | | |
|---|---|---|---|
| 5,211,654 A | | 5/1993 | Kaltenbach |
| 5,843,027 A | * | 12/1998 | Stone ...................... A61F 2/958 |
| | | | 604/509 |
| 5,882,334 A | * | 3/1999 | Sepetka ................ A61M 25/01 |
| | | | 604/164.08 |
| 5,919,163 A | | 7/1999 | Glickman |
| 6,409,652 B1 | | 6/2002 | Kamdar |
| 6,544,276 B1 | | 4/2003 | Azizi |
| 6,575,932 B1 | | 6/2003 | O'Brien et al. |
| 7,300,415 B2 | | 11/2007 | McMurtry et al. |
| 9,180,033 B2 | | 11/2015 | Motaganahalli |
| 9,345,864 B2 | | 5/2016 | Suehara |
| 9,398,965 B2 | | 7/2016 | Motaganahalli |
| 10,219,678 B2 | * | 3/2019 | Wake .................. A61B 1/00082 |
| 2007/0185444 A1 | * | 8/2007 | Euteneuer ......... A61M 25/1027 |
| | | | 604/96.01 |

(Continued)

FOREIGN PATENT DOCUMENTS

| | | |
|---|---|---|
| EP | 2589344 A1 | 5/2013 |
| WO | 2017/081561 A1 | 5/2017 |

*Primary Examiner* — Katherine M Shi
*Assistant Examiner* — Alyssa M Keane
(74) *Attorney, Agent, or Firm* — Troutman Pepper Hamilton Sanders LLP

(57) ABSTRACT

A balloon assist device is disclosed which includes an inner body, a balloon joined to the inner body, and a positioner. The inner body includes an open-ended closed tube extending along an axis from a proximal end to a distal end. The balloon assist device also includes an inflation tube in sealed communication with the balloon. The positioner allows a clinician to slide the balloon assist device along the catheter. The positioner may also include the inflation tube.

14 Claims, 5 Drawing Sheets

(56) References Cited

U.S. PATENT DOCUMENTS

| | | | |
|---|---|---|---|
| 2014/0343409 A1* | 11/2014 | Purtell | A61B 5/0084 |
| | | | 600/425 |
| 2015/0320982 A1 | 11/2015 | Massicotte | |
| 2016/0310759 A1 | 10/2016 | D'Andrea | |
| 2017/0106173 A1* | 4/2017 | Chanduszko | A61M 25/10 |
| 2017/0304595 A1* | 10/2017 | Nagasrinivasa | A61M 25/104 |

* cited by examiner

BALLOON ASSIST DEVICE AND METHOD FOR USING THE SAME

FIELD

This disclosure relates generally to the field of tools for vascular surgery. More particularly, it relates to balloon devices for occluding blood vessels during vascular surgery.

BACKGROUND

Balloon Guide Catheters facilitate the insertion of intravascular devices as well as control/restrict flow in ischemic applications. They are designed to have large lumens to maximize clot capture, and are indicated for use as a conduit for clot retrieval devices. Because the balloon is an integral part of the assembly on these devices, the profile of the devices is very large, for example 8F (2.7 mm) (French "F"=0.33 mm) as compared to a regular large ID guide catheter which might be sized 6 F (2.0 mm). Also, the overall flexibility of the system is decreased due to the required inflation lumen and dual layer construction needed to inflate the distal balloon. The combination of the large overall profile and the lack of distal flexibility makes tracking these devices in the neurovascular anatomy difficult. Accordingly, use of these devices is mostly limited to the proximal cerebral vasculature.

SUMMARY

To address these deficiencies in the existing art, a balloon assist device is disclosed which includes an inner body and a balloon joined to the inner body. In one example, the balloon assist device may include an inner body which includes an open-ended tube extending along an axis from a proximal end to a distal end, a balloon joined to the inner body, and a positioner extending from the balloon assist device in a proximal direction. The balloon may include a sheath of flexible material joined to the inner body with a volume between the sheath and the inner body forming the interior of the balloon. The sheath may be bonded to inner body along two perimeters which follow contours of an outer face of the inner body. The sheath may include an elastic or an inelastic material.

The balloon assist device includes an inflation tube in sealed communication with the balloon. In some examples, the positioner may include the inflation tube. The positioner may be attached to the inner body. The inner body may be configured to slide over the exterior of a catheter. The inner body is formed of a resilient material such as stainless steel or Nitinol. The positioner may be configured to position the balloon assist device in a proximal direction and in a distal direction.

A balloon assisted catheter system is also disclosed which includes a catheter and a balloon assist device, slidably engaging the outside of the catheter. The balloon assist device may include an inner body including an open-ended tube with a proximal and a distal end.

An inflatable balloon can be joined to the inner body, and a positioner extending in a proximal direction. The balloon assist device may also include an inflation tube in sealed communication with the inflatable sheath. The positioner of the balloon assisted catheter system may include the inflation tube. The positioner of the balloon assisted catheter system may be attached to the inner body and/or the balloon.

DETAILED DESCRIPTION

Figure 1:
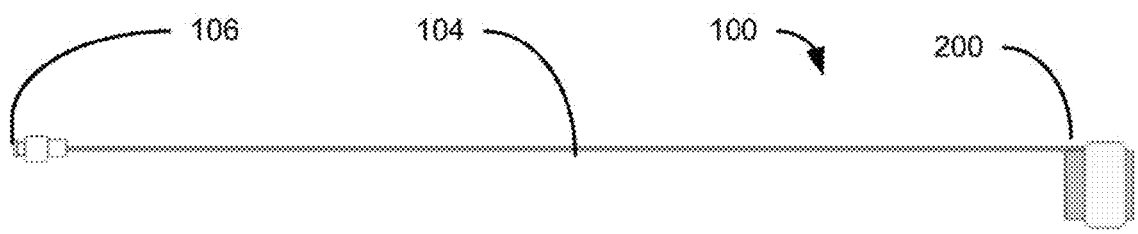
FIG. 1 is a diagram of a balloon assist device illustrating is basic components, in accordance with the present disclosure.
Figure 2:
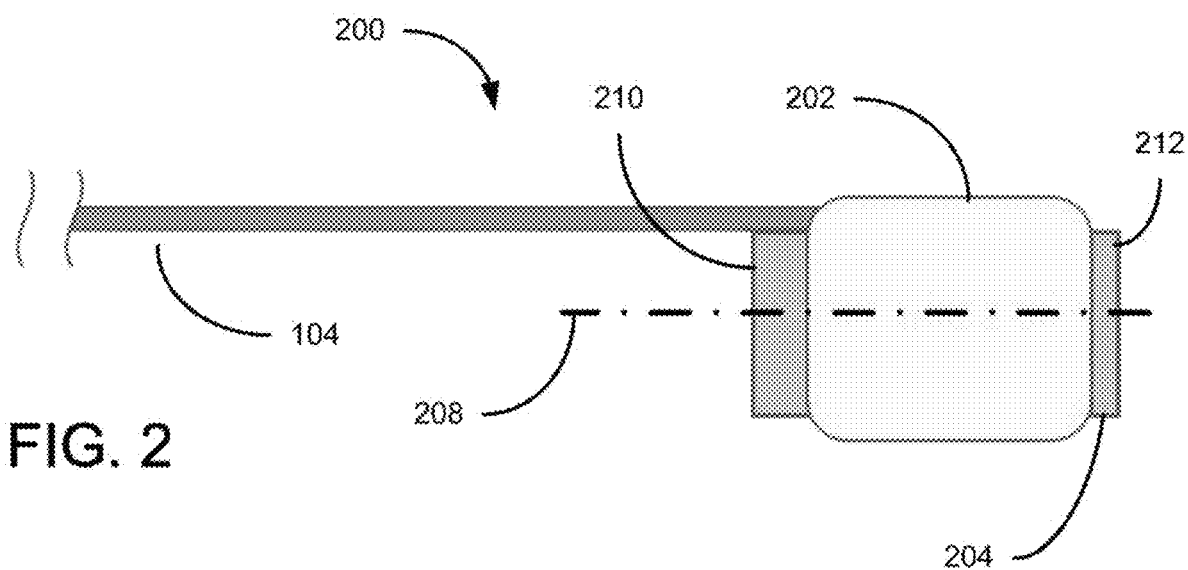
FIG. 2 is a diagram of the balloon assembly of the balloon assist device illustrating is construction, in accordance with the present disclosure.

Referring now to the Figures, in which like reference numerals represent like parts, various examples of the balloon assist device and methods of using it will be disclosed in detail. FIG. 1 is a diagram of the balloon assist device illustrating is basic components. The balloon assist device 100 includes a balloon assembly 200, an inflation tube 104, and an inflation port 106. FIG. 2 is a closer view of the balloon assembly 200. The balloon assembly 200 includes the balloon 202 fixed to an inner body 204. The inner body 204 extends along an axis 208 from a proximal end 210 to a distal end 212. The inner body 204 is a tube open at both ends 210, 212.

Figure 3:
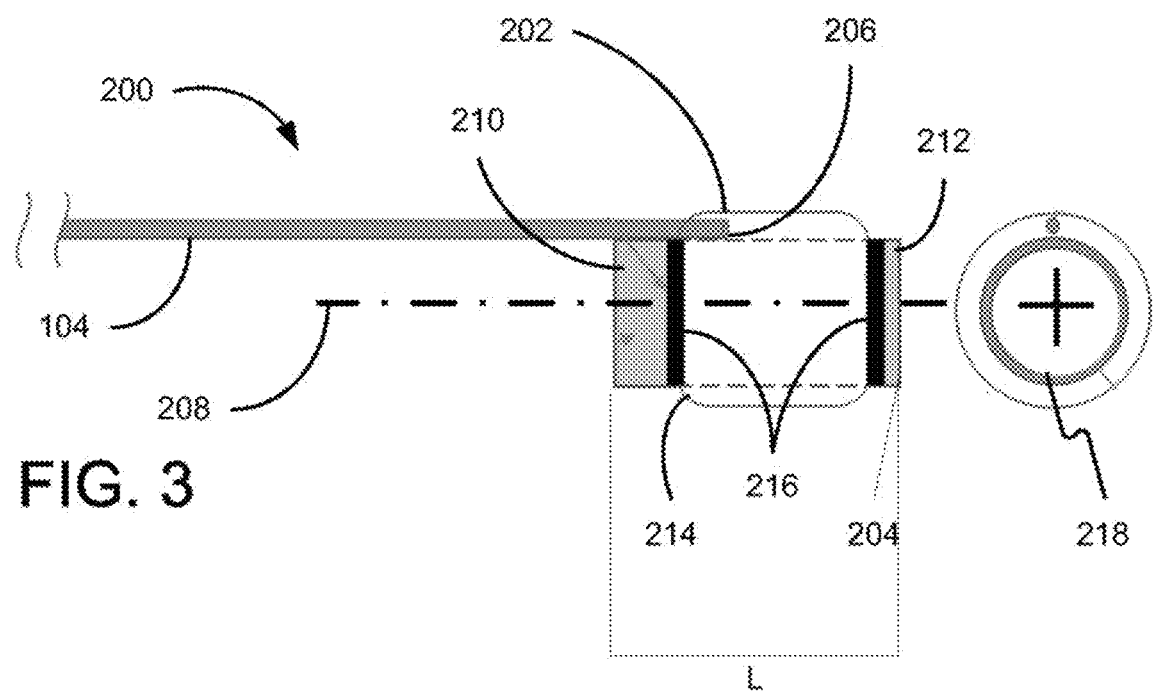
FIG. 3 is a diagram of the balloon assembly of the balloon assist device illustrating the balloon in the deflated state and highlighting the seals between the balloon and the inner body, in accordance with the present disclosure.
Figure 4:
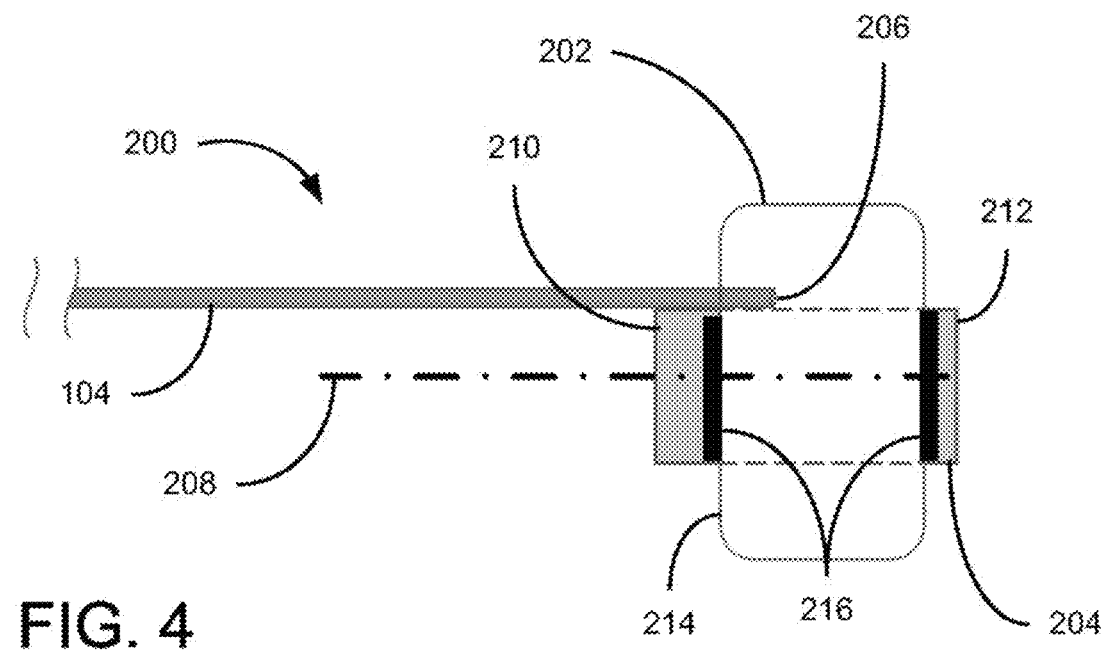
FIG. 4 is a diagram of the balloon assembly of the balloon assist device illustrating the balloon in the inflated state and highlighting the seals between the balloon and the inner body, in accordance with the present disclosure.

FIGS. 3 and 4 illustrate one example of attaching the balloon 202 to the inner body 204. In this example, the balloon 202 includes a sheath 214 of flexible material which is secured to the inner body 204 around the perimeter 216 of the sheath 214. In an alternate example, the inner body 204 can be formed integrally to the balloon 202. The sheath 214 may be made of an appropriate elastic or inelastic material, for example a polyimide. In this example, the volume enclosed between the sheath 214 and inner body 204 becomes the balloon 202. FIG. 3 illustrates the balloon 202 in the deflated state. FIG. 4 illustrates the balloon 202 in the inflated state. Although a particular shape of the balloon 202 is illustrated, the disclosure is not limited to the shape shown. The balloon 202 is inflated using the inflation tube 104. Sterile water, saline, or another appropriate solution may be introduced to the inflation tube 104 at the inflation port 106. The inflation port 106 may be one of several types known in the industry. The inflation tube 104 has an open end 206 which terminates inside the balloon 202. The outer perimeter of the inflation tube 104 is bonded to the sheath 214 and/or the inner body 204 at a location proximal to its open end 206. The bond provides a hermetic seal and a robust mechanical attachment to withstand forces during use of the balloon assist device 100.

In one example, the inner body 204 is made of a resilient material such as spring-temper stainless steel or, more preferably, a superelastic material Nitinol. The sheath 214 may be sealed to the inner body 204 using a variety of techniques well-known in the industry including, without limitation, adhesives, thermal bonding, and radio-frequency (RF) bonding. In addition to the seal between the sheath 214 and in the inner body 204, the inflation tube 104 is in sealed communication with the inner volume of the balloon 202.

The inflation tube 104 may be made from metal to facilitate pushability of the balloon 202 along the catheter 240, a polymeric material such as a polyimide for flexibility, or a combination of metal at the proximal end 210 and transitioning to the polymeric material as it extends toward the distal end 212. In some examples the inflation tube 104 may be used to position the balloon assist device 100 along the catheter 240 in the distal direction and to retract it in the proximal direction. In other examples, a separate positioner (not shown) may be attached to the inner body 204 to advance the balloon assist device 100 along the catheter 240 in the distal direction and to retract it in the proximal direction, allowing the inflation tube 104 to be more flexible. The positioner maybe made of a resilient material such as spring-temper stainless steel or, more preferably, a superelastic material such as Nitinol. The positioner may be attached to inner body 204, the balloon 202, or both. In several examples the positioner may be attached by welding, for example by laser or ultrasonic means, by adhesive, by crimping, or by thermal staking, as may be appropriate depending on the materials of the positioner, the inner body 204, and/or the balloon 202.

A length L of the balloon assembly 200 may be relatively short in the axial direction. In one example, the balloon assembly 200 may be less than or equal to twice the largest dimension of the interior of the inner body (e.g. an inner diameter 218 of the inner body 204). In another example, the balloon assembly may be less than or equal to the largest dimension of the interior of the inner body (e.g. an inner diameter 218 of the inner body 204). The short length L allows the balloon assembly 200 to track over tighter-radius bends of the catheter 240 which guides it. By bonding the balloon 202 to the inner body 204, the seal of the balloon 202 is independent of the catheter 240, unlike some designs which rely on a friction fit between the balloon 202 and the catheter 240.

The shape of the inner body 204, in examples, can be a closed tube or sleeve, and when engaged, partially surrounds the catheter 240 securely enough to track along catheter body inside the patient's vasculature during a procedure. The catheter 240 can be as small as 6-8 F, which enhances ability of the invention to access distal vasculature. In the example shown the inner body 204 has a cylindrical shape, but other cross-sections may be used as needed. In these examples, the inner body 204 is not slited or twisted, the balloon assist device 100 is designed to be "pre-loaded" on the catheter 240 before the catheter 240 is introduced into the patient.

Figure 5:
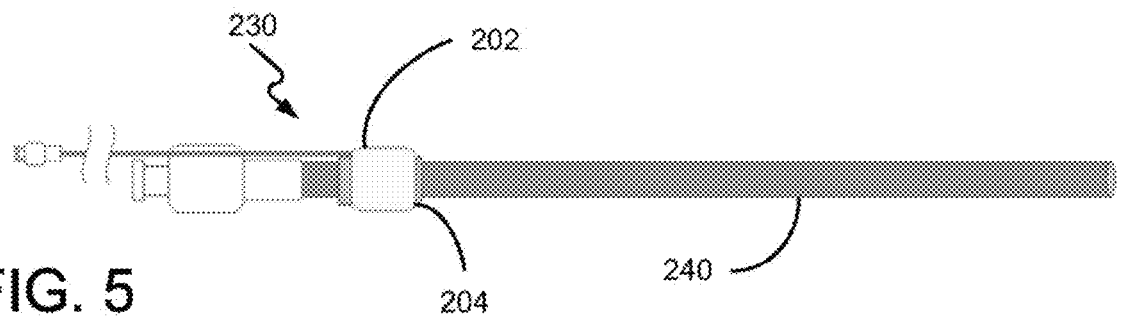
FIG. 5 is a diagram of the balloon assist device mounted on the proximal end of the catheter body, in accordance with the present disclosure.
Figure 6:
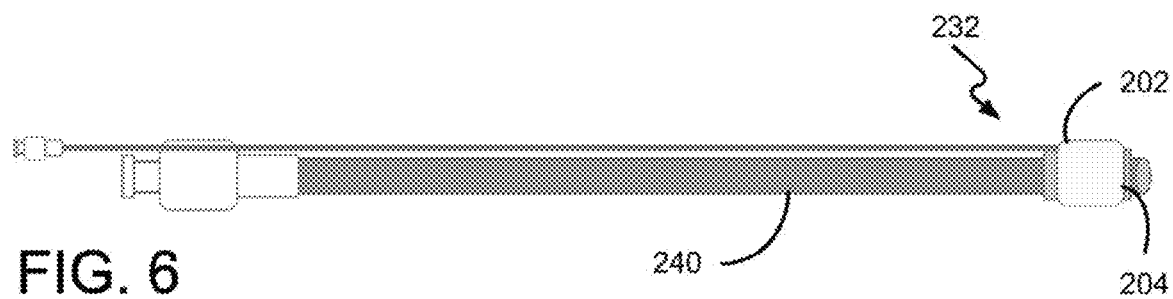
FIG. 6 is a diagram of the balloon assist device mounted on the catheter body and positioned at the distal end of the catheter, in accordance with the present disclosure.
Figure 7:
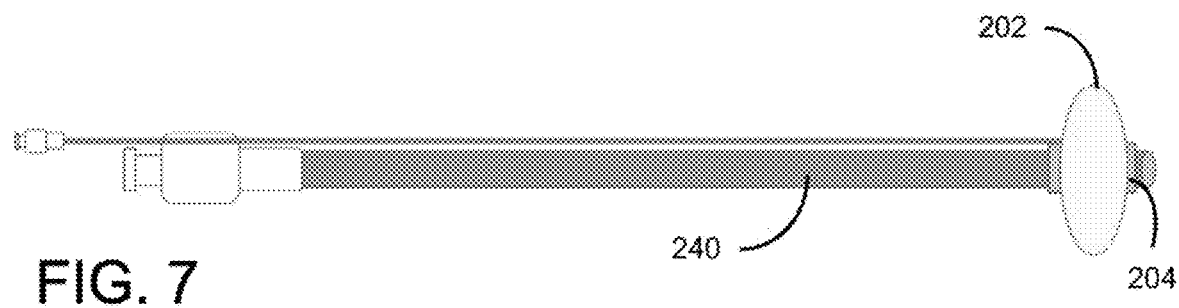
FIG. 7 is a diagram of the balloon assist device balloon inflated at the distal end of the catheter in accordance with the present disclosure.

FIGS. 5-7 show the basic operation of the balloon assist device 100. FIG. 5 shows the balloon assist device fully mounted on the catheter in a proximal position 230. The balloon assist device 100 is then slid distally along the catheter 240 using the inflation tube 104 or a separate positioner (not shown). FIG. 6 shows the balloon assist 100 mounted on the catheter 240 in the distal position 232 after sliding along the catheter 240. The balloon 202 is then inflated using the inflation tube 104, as shown in FIG. 7.

Figure 8:
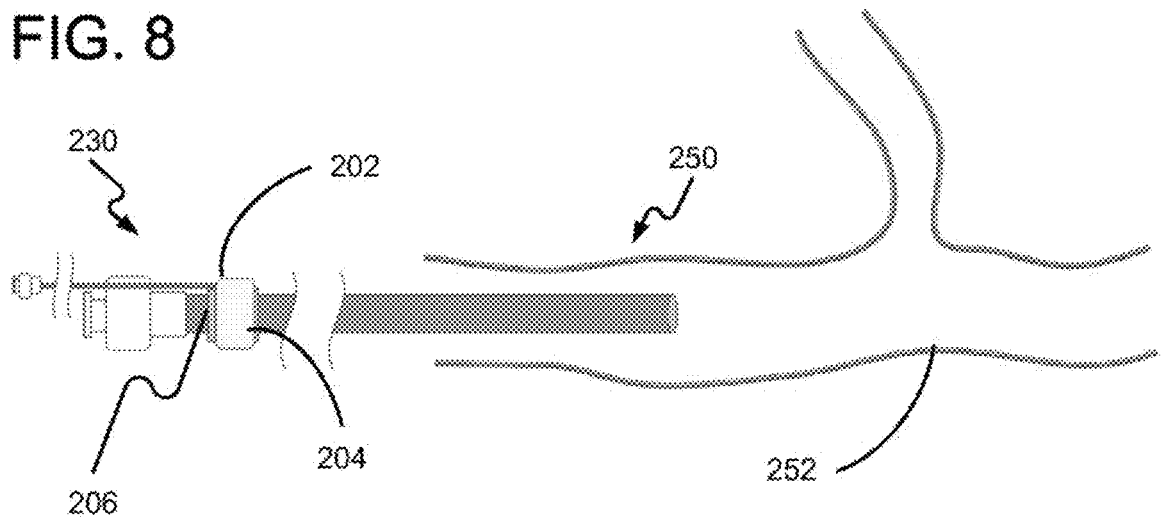
FIG. 8 is a diagram of a catheter positioned in a patient's vasculature with the balloon assist device mounted to the proximal end of the catheter body, in accordance with the present disclosure.
Figure 9:
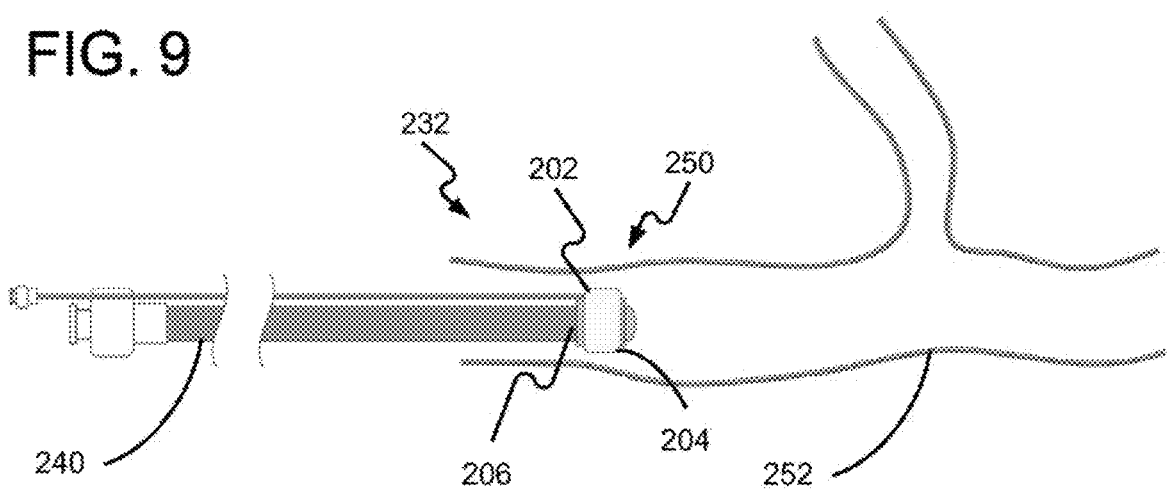
FIG. 9 is a diagram of a catheter positioned in a patient's vasculature with the balloon assist device positioned on the distal end of the catheter body at the treatment site, in accordance with the present disclosure.
Figure 10:
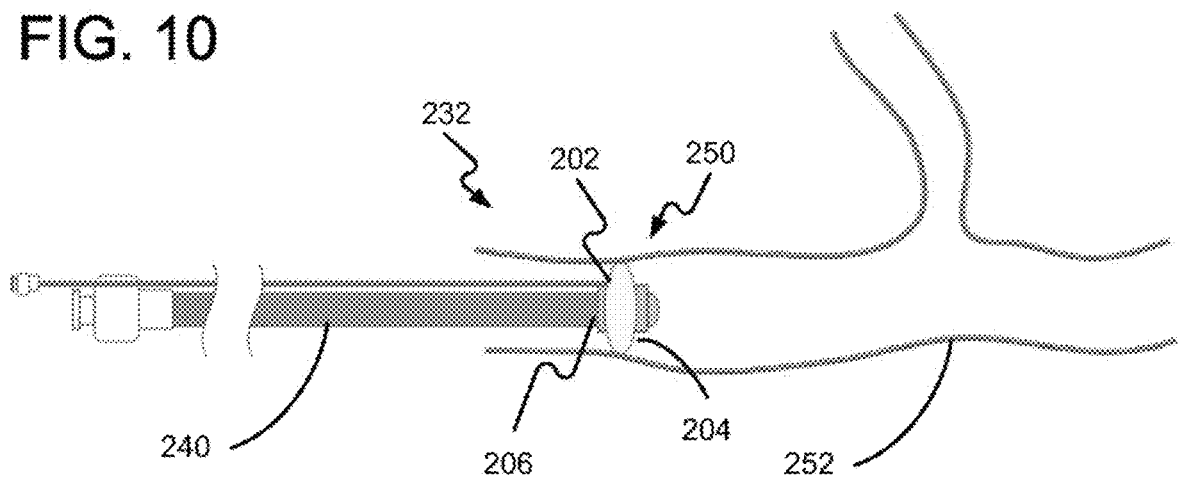
FIG. 10 is a diagram of a catheter positioned in a patient's vasculature with the balloon inflated at the treatment site, occluding a blood vessel, in accordance with the present disclosure.

FIGS. 8-10 show the basic operation of the balloon assist device 100 during a medical procedure. FIG. 8 shows the balloon assist device 100 fully mounted in the proximal position 230 on a catheter 240 which a clinician has already positioned at a treatment site 250 within a patient's vasculature 252. The balloon assist device 100 is then slid along the catheter 240 using the inflation tube 104 or a separate positioner (not shown) to treatment site 250. FIG. 9 shows the balloon assist device 100 mounted on the catheter 240 in the distal position 232 at the treatment site 250. The balloon 202 is then inflated using the inflation tube 104 to occlude part of the patient's vasculature 252, as shown in FIG. 10.

Figure 11:
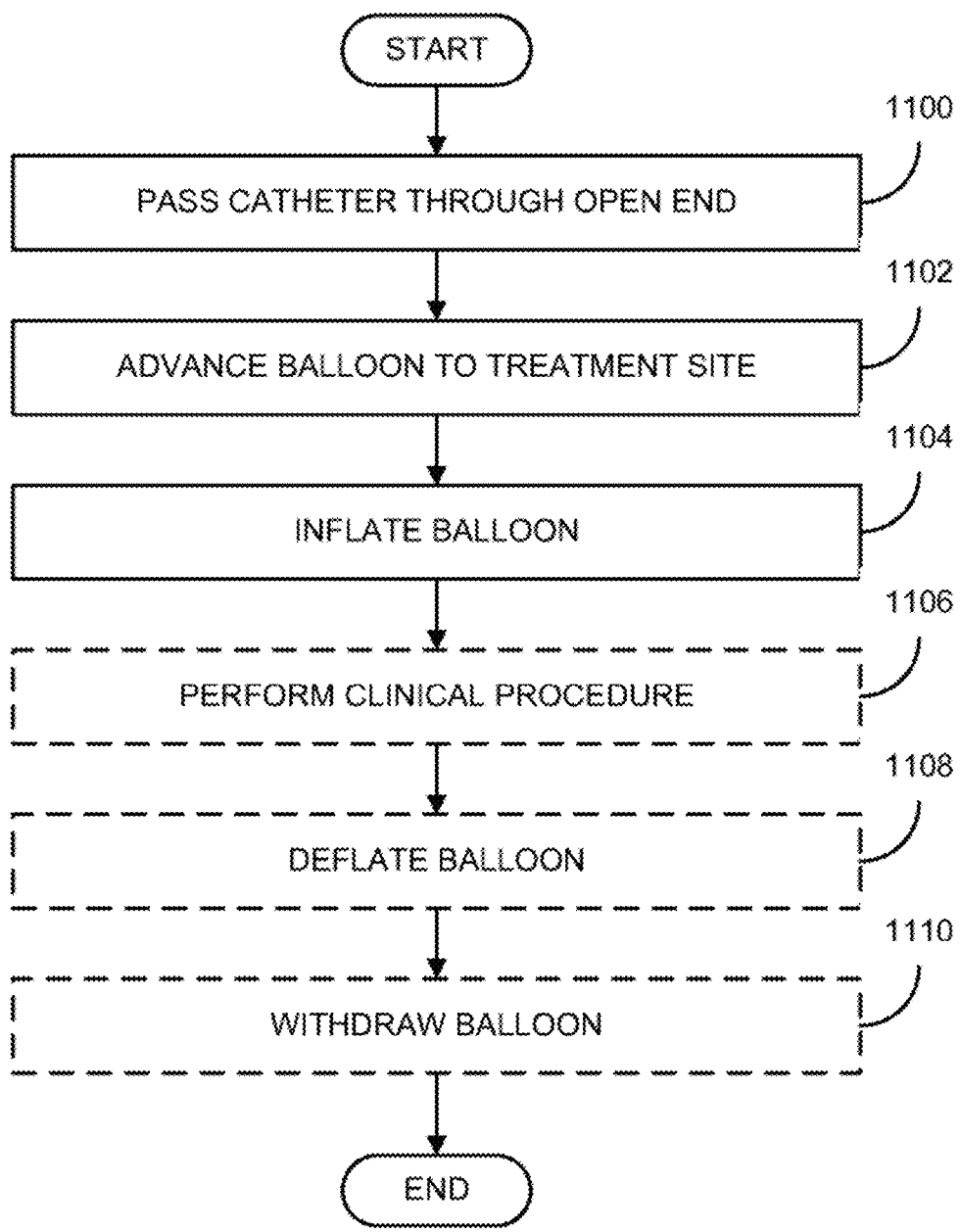
FIG. 11 is a flow chart illustrating one example of a method for using the balloon assist device, in accordance with the present disclosure.

FIG. 11 is flow chart showing the steps for using the balloon assist device. At 1100 the catheter 240 is inserted through the open end of the inner body 204. As illustrated, the inner body 204 is an open-ended closed tube, meaning that while the ends are open the circumference of the tube is complete and closed, there are no slits or openings in this example. At 1102 a positioner or inflation tube 104 is used to slide the balloon assist device 100 along the catheter 240 to a treatment site 250 in a patient's vasculature 252. In some examples the positioner may be the inflation tube 104. At 1104 the balloon assist device 100 is inflated at the treatment site 250 using the inflation tube 104. The remaining steps are optional based on the clinical procedure. At 1106 a procedure is performed while the inflated balloon assist device 100 occludes a blood vessel at the treatment site 250. At 1108 the balloon assist device 100 is deflated. At 1110 the deflated balloon assist device 100 is withdrawn.

To facilitate an understanding of the principals and features of the disclosed technology, illustrative examples are explained above. The components described hereinafter as making up various elements of the disclosed technology are intended to be illustrative and not restrictive. Many suitable components that would perform the same or similar functions as components described herein are intended to be embraced within the scope of the disclosed devices and methods. Such other components not described herein may include, but are not limited to, for example, components developed after development of the disclosed technology.

It must also be noted that, as used in the specification and the appended claims, the singular forms "a," "an" and "the" include plural referents unless the context clearly dictates otherwise. By "comprising" or "containing" or "including" is meant that at least the named component or method step is present in the article or method, but does not exclude the presence of other components or method steps, even if the other such components or method steps have the same function as what is named.

It is also to be understood that the mention of one or more method steps does not preclude the presence of additional method steps or intervening method steps between those steps expressly identified. Similarly, it is also to be understood that the mention of one or more components in a device or system does not preclude the presence of additional components or intervening components between those components expressly identified.

The design and functionality described in this application is intended to be exemplary in nature and is not intended to limit the instant disclosure in any way. Those having ordinary skill in the art will appreciate that the teachings of the disclosure may be implemented in a variety of suitable forms, including those forms disclosed herein and additional forms known to those having ordinary skill in the art.

Certain examples of this technology are described above with reference to flow diagrams. Some blocks of the block diagrams and flow diagrams may not necessarily need to be performed in the order presented, or may not necessarily need to be performed at all, according to some examples of the disclosure.

While certain examples of this disclosure have been described in connection with what is presently considered to be the most practical and various examples, it is to be understood that this disclosure is not to be limited to the disclosed examples, but on the contrary, is intended to cover various modifications and equivalent arrangements included within the scope of the appended claims. Although specific terms are employed herein, they are used in a generic and descriptive sense only and not for purposes of limitation.

This written description uses examples to disclose certain examples of the technology and also to enable any person skilled in the art to practice certain examples of this technology, including making and using any apparatuses or systems and performing any incorporated methods. The patentable scope of certain examples of the technology is defined in the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The invention claimed is:

1. A balloon assisted catheter system comprising:
    a catheter; and
    a balloon assist device comprising:
        an inner body comprising an open-ended closed tube extending along an axis from a proximal end to a distal end;
        a balloon joined to the inner body and comprising an axial length shorter than an axial length of the inner body; and
        an inflation tube, separate and distinct from the inner body, having an open end disposed within the balloon, extending from the proximal end of the inner body in a proximal direction, configured to inflate and deflate the balloon, pushable to move the inner body from approximate a proximal end of a catheter, over an outer surface of the catheter to approximate a distal end of the catheter, and pullable to move the inner body from approximate the distal end of the catheter, over the outer surface of the catheter to approximate the proximal end of the catheter.

2. The balloon assisted catheter system of claim 1 wherein the balloon comprises a sheath of flexible material bonded to the inner body and a volume between the sheath and the inner body which comprises an interior of the balloon.

3. The balloon assisted catheter system of claim 2 wherein the sheath is joined to inner body along two perimeters which follow contours of an outer face of the inner body.

4. The balloon assisted catheter system of claim 2 wherein the sheath comprises an elastic material.

5. The balloon assisted catheter system of claim 2 wherein the sheath comprises an inelastic material.

6. The balloon assisted catheter system of claim 1 wherein the inflation tube is attached to an outer surface of the inner body.

7. The balloon assisted catheter system of claim 1 wherein the inner body is formed of a resilient material.

8. A balloon assisted catheter system comprising:
    a catheter having a proximal end, a distal end, and an outer surface therebetween; and
    a balloon assist device, slidably engaging an outside of the catheter, comprising:
        an inner body comprising an open-ended closed tube having a proximal and a distal end, the inner body surrounding the catheter and configured to proximally and distally slide over the outside of the catheter;
        an inflatable balloon joined to the inner body, the inflatable balloon comprising an axial length shorter than an axial length of the inner body; and
        an inflation tube separate and distinct from the inner body and configured to inflate and deflate the balloon and configured to move the balloon along the catheter from approximate the proximal end, over the outer surface to approximate the distal end.

9. The balloon assisted catheter system of claim 8 wherein the inflation tube is attached to the inner body.

10. The balloon assisted catheter system of claim 8 wherein the inflation tube is attached to the balloon.

11. A method of using a balloon assisted catheter system, the method comprising:
    mounting a balloon assist device on an outer surface of a proximal end of a catheter, such that an open-ended closed tubular body having a proximal and a distal end of the balloon assist device surrounds the catheter and slides proximally and distally over the outside of the catheter;
    pushing an inflation tube of the balloon assist device to thereby slide the balloon assist device over the outside of the catheter from the proximal end of the catheter to a distal end of the catheter, the inflation tube being separate and distinct from the inner body;
    inflating, via the inflation tube, an inflatable balloon joined to an outer surface of the inner body of the balloon assist device and comprising an axial length shorter than an axial length of the inner body;
    at least partially occluding a patient's blood vessel as a result of inflating the inflatable balloon; and
    deflating the balloon using the inflation tube.

12. The method of claim 11, wherein mounting the balloon assist device on the proximal end of the catheter comprises inserting the catheter through an open end of the inner body.

13. The method of claim 11, further comprising performing a clinical procedure while the balloon is inflated.

14. The method of claim 11, further comprising withdrawing the balloon from the patient.

* * * * *